US009339362B2

(12) United States Patent
Goldberg et al.

(10) Patent No.: US 9,339,362 B2
(45) Date of Patent: May 17, 2016

(54) APPARATUS AND METHOD FOR SUSPENDING A UTERUS

(75) Inventors: Roger P. Goldberg, Evanston, IL (US); Dennis Miller, Whitefish Bay, WI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 311 days.

(21) Appl. No.: 12/983,666

(22) Filed: Jan. 3, 2011

(65) Prior Publication Data

US 2011/0098527 A1    Apr. 28, 2011

Related U.S. Application Data

(63) Continuation of application No. 11/535,901, filed on Sep. 27, 2006, now Pat. No. 7,878,970.

(60) Provisional application No. 60/721,366, filed on Sep. 28, 2005.

(51) Int. Cl.
*A61F 2/00* (2006.01)
*A61B 17/42* (2006.01)
*A61B 17/04* (2006.01)

(52) U.S. Cl.
CPC ............ *A61F 2/0045* (2013.01); *A61B 17/4241* (2013.01); *A61B 17/0401* (2013.01)

(58) Field of Classification Search
CPC .................. A61B 17/0401; A61B 2017/0406; A61B 2017/00805; A61F 2/004; A61F 2/0031; A61F 2/0036; A61F 2/0045; A61F 2/0063; A61F 2/0077; A61F 2002/0068; A61F 2002/0072
USPC .......................... 600/37, 29–32; 606/151, 119
See application file for complete search history.

(56) References Cited

U.S. PATENT DOCUMENTS

| 669,034 A | 2/1901 | Manly |
| 2,687,131 A | 8/1954 | Raiche |
| 3,123,077 A | 3/1964 | Alcamo |
| 4,083,369 A | 4/1978 | Sinnreich |

(Continued)

FOREIGN PATENT DOCUMENTS

| DE | 10056169 A1 | 6/2002 |
| EP | 0088714 A1 | 9/1983 |

(Continued)

OTHER PUBLICATIONS

Non-Final Office Action for U.S. Appl. No. 11/686,683, mailed on Jul. 8, 2009, 13 pages.

(Continued)

*Primary Examiner* — Charles A Marmor, II
*Assistant Examiner* — Carrie R Dorna
(74) *Attorney, Agent, or Firm* — Brake Hughes Bellermann LLP

(57) ABSTRACT

An inter-vaginal device for performing a uterine suspension includes a rigid body for manipulating the uterus and implanting a suspension member, such as a mesh, for securing the uterus to an anchoring site (e.g., into a pelvic muscle or ligament). In one embodiment, a method includes inserting at least a portion of a uterine suspension member through an anterior or posterior vaginal incision. An end of the suspension member is anchored to a selected portion of a pelvic tissue. At least a portion of the suspension member is attached to a vaginal apex. A uterine manipulator is advanced in a direction toward the selected portion of the pelvic tissue such that at least a portion of a uterus is moved upward.

13 Claims, 5 Drawing Sheets

(56) References Cited

U.S. PATENT DOCUMENTS

| | | |
|---|---|---|
| 4,324,331 A | 4/1982 | Ignasiak |
| 4,792,336 A | 12/1988 | Hlavacek et al. |
| 4,919,667 A | 4/1990 | Richmond |
| 4,979,956 A | 12/1990 | Silvestrini |
| 4,998,912 A | 3/1991 | Scarbrough et al. |
| 5,013,292 A | 5/1991 | Lemay |
| 5,082,112 A | 1/1992 | Dunklee |
| 5,112,344 A | 5/1992 | Petros |
| 5,149,329 A | 9/1992 | Richardson |
| 5,217,466 A | 6/1993 | Hasson |
| 5,217,486 A | 6/1993 | Rice et al. |
| 5,217,494 A | 6/1993 | Coggins et al. |
| 5,219,359 A * | 6/1993 | McQuilkin ........ A61B 17/0401 602/43 |
| 5,263,969 A | 11/1993 | Phillips |
| 5,356,432 A | 10/1994 | Rutkow et al. |
| 5,362,294 A | 11/1994 | Seitzinger |
| 5,364,408 A | 11/1994 | Gordon |
| 5,383,905 A | 1/1995 | Golds et al. |
| 5,405,359 A | 4/1995 | Pierce |
| 5,425,747 A | 6/1995 | Brotz |
| 5,451,235 A | 9/1995 | Lock et al. |
| 5,458,609 A | 10/1995 | Gordon et al. |
| 5,458,636 A | 10/1995 | Brancato |
| 5,464,409 A * | 11/1995 | Mohajer ...................... 606/119 |
| 5,485,917 A | 1/1996 | Early |
| 5,527,341 A | 6/1996 | Gogolewski et al. |
| 5,534,008 A | 7/1996 | Acksel |
| 5,540,704 A | 7/1996 | Gordon et al. |
| 5,562,689 A | 10/1996 | Green et al. |
| 5,569,283 A | 10/1996 | Green et al. |
| 5,575,800 A | 11/1996 | Gordon |
| 5,578,044 A | 11/1996 | Gordon et al. |
| 5,584,859 A | 12/1996 | Brotz |
| 5,611,515 A | 3/1997 | Benderev et al. |
| 5,643,311 A | 7/1997 | Smith et al. |
| 5,662,664 A | 9/1997 | Gordon et al. |
| 5,683,402 A | 11/1997 | Cosgrove et al. |
| 5,700,272 A | 12/1997 | Gordon et al. |
| 5,702,397 A | 12/1997 | Goble et al. |
| 5,713,910 A | 2/1998 | Gordon et al. |
| 5,720,761 A | 2/1998 | Kaali |
| 5,741,277 A | 4/1998 | Gordon et al. |
| 5,741,279 A | 4/1998 | Gordon et al. |
| 5,741,299 A | 4/1998 | Rudt |
| 5,840,011 A | 11/1998 | Landgrebe et al. |
| 5,871,488 A | 2/1999 | Tovey et al. |
| 5,899,909 A | 5/1999 | Claren et al. |
| 5,922,826 A | 7/1999 | Kuze et al. |
| 5,931,855 A | 8/1999 | Buncke |
| 5,948,001 A | 9/1999 | Larsen |
| 5,976,127 A | 11/1999 | Lax |
| 5,988,549 A | 11/1999 | Hitomi et al. |
| 6,010,447 A | 1/2000 | Kardjian |
| 6,012,580 A | 1/2000 | Peters et al. |
| 6,039,686 A | 3/2000 | Kovac |
| 6,042,534 A | 3/2000 | Gellman et al. |
| 6,042,536 A | 3/2000 | Tihon et al. |
| 6,042,592 A | 3/2000 | Schmitt |
| 6,044,847 A | 4/2000 | Carter et al. |
| 6,048,351 A | 4/2000 | Gordon et al. |
| 6,096,051 A | 8/2000 | Kortenbach et al. |
| 6,102,921 A | 8/2000 | Zhu et al. |
| 6,195,646 B1 | 2/2001 | Grosh et al. |
| 6,197,036 B1 | 3/2001 | Tripp et al. |
| 6,200,330 B1 | 3/2001 | Benderev et al. |
| 6,221,005 B1 | 4/2001 | Bruckner et al. |
| 6,224,616 B1 | 5/2001 | Kugel |
| 6,267,772 B1 | 7/2001 | Mulhauser et al. |
| 6,273,852 B1 | 8/2001 | Lehe et al. |
| 6,306,079 B1 | 10/2001 | Trabucco |
| 6,322,492 B1 | 11/2001 | Kovac |
| 6,328,686 B1 | 12/2001 | Kovac |
| 6,346,111 B1 | 2/2002 | Gordon et al. |
| 6,375,662 B1 | 4/2002 | Schmitt |
| 6,382,214 B1 | 5/2002 | Raz et al. |
| 6,406,423 B1 | 6/2002 | Scetbon |
| 6,454,778 B2 | 9/2002 | Kortenbach |
| 6,478,727 B2 | 11/2002 | Scetbon |
| 6,491,703 B1 | 12/2002 | Ulmsten |
| 6,502,578 B2 | 1/2003 | Raz et al. |
| 6,506,190 B1 | 1/2003 | Walshe |
| 6,530,943 B1 | 3/2003 | Hoepffner et al. |
| 6,544,273 B1 | 4/2003 | Harari et al. |
| 6,547,800 B2 | 4/2003 | Foerster et al. |
| 6,551,329 B1 | 4/2003 | Kortenbach et al. |
| 6,565,580 B1 | 5/2003 | Beretta |
| 6,575,897 B1 | 6/2003 | Ory et al. |
| 6,575,998 B2 | 6/2003 | Beyar |
| 6,582,443 B2 | 6/2003 | Cabak et al. |
| 6,592,515 B2 | 7/2003 | Thierfelder et al. |
| 6,592,610 B2 | 7/2003 | Beyar et al. |
| 6,595,911 B2 | 7/2003 | LoVuolo |
| 6,596,001 B2 | 7/2003 | Stormby et al. |
| 6,599,235 B2 | 7/2003 | Kovac |
| 6,599,310 B2 | 7/2003 | Leung et al. |
| 6,612,977 B2 | 9/2003 | Staskin et al. |
| 6,638,209 B2 | 10/2003 | Landgrebe |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,641,525 B2 | 11/2003 | Rocheleau et al. |
| 6,648,899 B2 | 11/2003 | Kalinski et al. |
| 6,648,921 B2 | 11/2003 | Anderson et al. |
| 6,652,450 B2 | 11/2003 | Neisz et al. |
| 6,666,817 B2 | 12/2003 | Li |
| 6,669,706 B2 | 12/2003 | Schmitt et al. |
| 6,669,735 B1 | 12/2003 | Pelissier |
| 6,673,010 B2 | 1/2004 | Skiba et al. |
| 6,691,711 B2 | 2/2004 | Raz et al. |
| 6,695,855 B1 | 2/2004 | Gaston |
| 6,702,827 B1 | 3/2004 | Lund et al. |
| 6,730,110 B1 | 5/2004 | Harari et al. |
| 6,746,455 B2 | 6/2004 | Beyar et al. |
| 6,752,814 B2 | 6/2004 | Gellman et al. |
| 6,755,781 B2 | 6/2004 | Gellman |
| 6,808,487 B2 | 10/2004 | Migliari |
| 6,830,052 B2 | 12/2004 | Carter et al. |
| 6,848,152 B2 | 2/2005 | Genova et al. |
| 6,872,227 B2 | 3/2005 | Sump et al. |
| 6,881,184 B2 | 4/2005 | Zappala |
| 6,890,338 B1 | 5/2005 | Davis et al. |
| 6,908,425 B2 | 6/2005 | Luscombe |
| 6,911,003 B2 | 6/2005 | Anderson et al. |
| 6,911,034 B2 | 6/2005 | Nobles et al. |
| 6,932,759 B2 | 8/2005 | Kammerer et al. |
| 6,936,052 B2 | 8/2005 | Gellman et al. |
| 6,936,054 B2 | 8/2005 | Chu |
| 6,936,952 B2 | 8/2005 | Takamine |
| 6,946,003 B1 | 9/2005 | Wolowacz et al. |
| 6,953,428 B2 | 10/2005 | Gellman et al. |
| 6,960,160 B2 | 11/2005 | Browning |
| 6,971,986 B2 | 12/2005 | Staskin et al. |
| 6,986,780 B2 | 1/2006 | Rudnick et al. |
| 6,991,597 B2 | 1/2006 | Gellman et al. |
| 7,011,688 B2 | 3/2006 | Gryska et al. |
| 7,025,772 B2 | 4/2006 | Gellman et al. |
| 7,048,682 B2 | 5/2006 | Neisz et al. |
| 7,056,333 B2 | 6/2006 | Walshe |
| 7,070,556 B2 | 7/2006 | Anderson et al. |
| 7,070,558 B2 | 7/2006 | Gellman et al. |
| 7,083,568 B2 | 8/2006 | Neisz et al. |
| 7,083,637 B1 | 8/2006 | Tannhauser |
| 7,090,686 B2 | 8/2006 | Nobles et al. |
| 7,094,199 B2 | 8/2006 | Petros et al. |
| 7,112,171 B2 | 9/2006 | Rocheleau et al. |
| 7,112,210 B2 | 9/2006 | Ulmsten et al. |
| 7,122,039 B2 | 10/2006 | Chu |
| 7,131,943 B2 | 11/2006 | Kammerer |
| 7,131,944 B2 | 11/2006 | Jacquetin |
| 7,198,597 B2 | 4/2007 | Siegel et al. |
| 7,204,801 B2 | 4/2007 | Grocela |
| 7,204,802 B2 | 4/2007 | De Leval |

(56) References Cited

U.S. PATENT DOCUMENTS

| | | |
|---|---|---|
| 7,223,229 B2 | 5/2007 | Inman et al. |
| 7,226,407 B2 | 6/2007 | Kammerer et al. |
| 7,226,408 B2 | 6/2007 | Harai et al. |
| 7,229,453 B2 | 6/2007 | Anderson et al. |
| 7,235,043 B2 | 6/2007 | Gellman et al. |
| 7,244,260 B2 | 7/2007 | Koseki |
| 7,244,759 B2 | 7/2007 | Muller et al. |
| 7,267,645 B2 | 9/2007 | Anderson et al. |
| 7,291,104 B2 | 11/2007 | Neisz et al. |
| 7,351,197 B2 | 4/2008 | Montpetit et al. |
| 7,361,138 B2 | 4/2008 | Wagner et al. |
| 7,364,541 B2 | 4/2008 | Chu et al. |
| 7,402,133 B2 | 7/2008 | Chu et al. |
| 7,413,540 B2 | 8/2008 | Gellman et al. |
| 7,527,588 B2 | 5/2009 | Zaddem et al. |
| 8,128,552 B2 | 3/2012 | O'Donnell |
| 8,911,348 B2 | 12/2014 | Goldberg et al. |
| 2001/0023356 A1 | 9/2001 | Raz et al. |
| 2001/0049467 A1 | 12/2001 | Lehe et al. |
| 2002/0010457 A1 | 1/2002 | Duchon et al. |
| 2002/0028980 A1 | 3/2002 | Thierfelder et al. |
| 2002/0099259 A1 | 7/2002 | Anderson et al. |
| 2002/0128670 A1 | 9/2002 | Ulmsten et al. |
| 2002/0133236 A1 | 9/2002 | Rousseau |
| 2002/0143234 A1 | 10/2002 | LoVuolo |
| 2002/0147382 A1* | 10/2002 | Neisz et al. ............... 600/29 |
| 2002/0151909 A1 | 10/2002 | Gellman et al. |
| 2002/0156489 A1 | 10/2002 | Gellman et al. |
| 2003/0009181 A1 | 1/2003 | Gellman et al. |
| 2003/0023138 A1 | 1/2003 | Luscombe |
| 2003/0023250 A1 | 1/2003 | Watschke et al. |
| 2003/0050530 A1 | 3/2003 | Neisz et al. |
| 2003/0055313 A1 | 3/2003 | Anderson et al. |
| 2003/0078604 A1 | 4/2003 | Walshe |
| 2003/0125715 A1 | 7/2003 | Kuehn et al. |
| 2003/0149334 A1 | 8/2003 | Ulmsten et al. |
| 2003/0176762 A1 | 9/2003 | Kammerer |
| 2003/0191360 A1 | 10/2003 | Browning |
| 2003/0208208 A1 | 11/2003 | Chu |
| 2003/0220538 A1 | 11/2003 | Jacquetin |
| 2003/0225424 A1 | 12/2003 | Benderev |
| 2003/0233107 A1 | 12/2003 | Gellman et al. |
| 2003/0233108 A1 | 12/2003 | Gellman et al. |
| 2004/0006353 A1 | 1/2004 | Bosley et al. |
| 2004/0015048 A1 | 1/2004 | Neisz et al. |
| 2004/0015177 A1 | 1/2004 | Chu |
| 2004/0034372 A1 | 2/2004 | Chu |
| 2004/0039246 A1* | 2/2004 | Gellman et al. ........... 600/30 |
| 2004/0039453 A1 | 2/2004 | Anderson et al. |
| 2004/0059293 A1 | 3/2004 | Chu et al. |
| 2004/0068159 A1 | 4/2004 | Neisz et al. |
| 2004/0073234 A1 | 4/2004 | Chu et al. |
| 2004/0087970 A1 | 5/2004 | Chu et al. |
| 2004/0106847 A1 | 6/2004 | Benderev |
| 2004/0116944 A1 | 6/2004 | Chu et al. |
| 2004/0133217 A1 | 7/2004 | Watschke |
| 2004/0138747 A1* | 7/2004 | Kaladelfos ............. 623/13.13 |
| 2004/0181243 A1 | 9/2004 | Chu et al. |
| 2004/0186515 A1 | 9/2004 | Rosenblatt |
| 2004/0225181 A1 | 11/2004 | Chu et al. |
| 2004/0230206 A1 | 11/2004 | Gellman et al. |
| 2004/0231678 A1 | 11/2004 | Fierro |
| 2004/0236356 A1 | 11/2004 | Rioux et al. |
| 2004/0249397 A1 | 12/2004 | Delorme et al. |
| 2004/0249473 A1 | 12/2004 | Delorme et al. |
| 2005/0004427 A1 | 1/2005 | Cervigni |
| 2005/0004576 A1 | 1/2005 | Benderev |
| 2005/0038451 A1 | 2/2005 | Rao et al. |
| 2005/0038452 A1 | 2/2005 | Chu |
| 2005/0075660 A1 | 4/2005 | Chu et al. |
| 2005/0080317 A1 | 4/2005 | Merade |
| 2005/0090706 A1 | 4/2005 | Gellman et al. |
| 2005/0096499 A1 | 5/2005 | Li et al. |
| 2005/0101834 A1 | 5/2005 | Merade |
| 2005/0107805 A1 | 5/2005 | Bouffier et al. |
| 2005/0131391 A1 | 6/2005 | Chu et al. |
| 2005/0131392 A1 | 6/2005 | Chu et al. |
| 2005/0131393 A1 | 6/2005 | Chu et al. |
| 2005/0177022 A1 | 8/2005 | Chu et al. |
| 2005/0192600 A1 | 9/2005 | Nicolo et al. |
| 2005/0222589 A1 | 10/2005 | Chu |
| 2005/0222591 A1 | 10/2005 | Gingras et al. |
| 2005/0234291 A1 | 10/2005 | Gingras |
| 2005/0245787 A1 | 11/2005 | Cox et al. |
| 2005/0250977 A1 | 11/2005 | Montpetit et al. |
| 2005/0250978 A1 | 11/2005 | Kammerer |
| 2005/0256366 A1 | 11/2005 | Chu |
| 2005/0256530 A1 | 11/2005 | Petros |
| 2005/0261545 A1 | 11/2005 | Gellman et al. |
| 2005/0261547 A1 | 11/2005 | Bouffier |
| 2005/0277807 A1 | 12/2005 | MacLean et al. |
| 2005/0278037 A1 | 12/2005 | Delorme et al. |
| 2006/0015001 A1 | 1/2006 | Staskin et al. |
| 2006/0025649 A1 | 2/2006 | Smith et al. |
| 2006/0025783 A1 | 2/2006 | Smith et al. |
| 2006/0041185 A1 | 2/2006 | Browning |
| 2006/0041263 A1 | 2/2006 | Chu et al. |
| 2006/0052801 A1 | 3/2006 | Dreyfuss et al. |
| 2006/0058574 A1 | 3/2006 | Priewe et al. |
| 2006/0058575 A1 | 3/2006 | Zaddem et al. |
| 2006/0069301 A1 | 3/2006 | Neisz et al. |
| 2006/0089524 A1 | 4/2006 | Chu |
| 2006/0089525 A1 | 4/2006 | Mamo et al. |
| 2006/0122457 A1 | 6/2006 | Kovac et al. |
| 2006/0173237 A1 | 8/2006 | Jacquetin |
| 2006/0205995 A1 | 9/2006 | Browning |
| 2006/0211911 A1 | 9/2006 | Jao et al. |
| 2006/0229493 A1 | 10/2006 | Weiser et al. |
| 2006/0229596 A1* | 10/2006 | Weiser et al. ............... 606/37 |
| 2006/0264698 A1 | 11/2006 | Kondonis et al. |
| 2007/0043255 A1 | 2/2007 | O'Donnell |
| 2007/0055095 A1 | 3/2007 | Chu et al. |
| 2007/0161849 A1 | 7/2007 | Goldberg |
| 2007/0173864 A1 | 7/2007 | Chu |
| 2007/0270890 A1 | 11/2007 | Miller |
| 2007/0276358 A1 | 11/2007 | Barzell et al. |
| 2008/0177132 A1 | 7/2008 | Alinsod et al. |
| 2008/0234543 A1 | 9/2008 | Goldwasser |
| 2009/0171142 A1 | 7/2009 | Chu |
| 2009/0171143 A1 | 7/2009 | Chu et al. |
| 2010/0130814 A1 | 5/2010 | Dubernard |
| 2010/0152530 A1 | 6/2010 | Timmer et al. |
| 2011/0112357 A1 | 5/2011 | Chapman et al. |
| 2012/0136324 A1 | 5/2012 | Hanuka et al. |
| 2013/0066145 A1 | 3/2013 | Fairneny et al. |
| 2015/0094527 A1 | 4/2015 | Goldberg et al. |

FOREIGN PATENT DOCUMENTS

| | | |
|---|---|---|
| EP | 0141589 A1 | 5/1985 |
| EP | 0299158 A1 | 1/1989 |
| EP | 0362146 A1 | 4/1990 |
| EP | 0412664 A1 | 2/1991 |
| EP | 0567130 A1 | 10/1993 |
| EP | 0774240 A1 | 5/1997 |
| EP | 1201189 A2 | 5/2002 |
| EP | 1508305 A2 | 2/2005 |
| EP | 1520554 A2 | 4/2005 |
| EP | 1609439 A1 | 12/2005 |
| EP | 1933786 A2 | 6/2008 |
| EP | 2617385 A2 | 7/2013 |
| EP | 1998711 B1 | 12/2013 |
| FR | 2785521 A1 | 5/2000 |
| FR | 2852817 A1 | 10/2004 |
| FR | 2852818 | 10/2004 |
| FR | 2871365 | 12/2005 |
| GB | 670349 | 4/1952 |
| JP | 06114067 A2 | 4/1994 |
| JP | 08117239 A2 | 5/1996 |
| MX | PA04008407 A | 12/2005 |
| WO | 96/09796 A2 | 4/1996 |
| WO | 96/39948 A1 | 12/1996 |
| WO | 98/35616 A1 | 8/1998 |
| WO | 98/35632 A1 | 8/1998 |

(56) References Cited

FOREIGN PATENT DOCUMENTS

| | | |
|---|---|---|
| WO | 98/43545 A1 | 10/1998 |
| WO | 99/37216 A1 | 7/1999 |
| WO | 00/09039 A1 | 2/2000 |
| WO | 00/74613 A1 | 12/2000 |
| WO | 0074594 A1 | 12/2000 |
| WO | 01/06951 A1 | 2/2001 |
| WO | 01/52135 A1 | 7/2001 |
| WO | 02/31681 A1 | 4/2002 |
| WO | 02/32284 A2 | 4/2002 |
| WO | 02/38079 A2 | 5/2002 |
| WO | 02/058563 A1 | 8/2002 |
| WO | 02/062237 A1 | 8/2002 |
| WO | 02/078571 A2 | 10/2002 |
| WO | 03/068107 A1 | 8/2003 |
| WO | 03/073960 A1 | 9/2003 |
| WO | 03/092546 A2 | 11/2003 |
| WO | 03/096928 A1 | 11/2003 |
| WO | 03/096929 A1 | 11/2003 |
| WO | 2004001619 A1 | 12/2003 |
| WO | 2004/012626 A1 | 2/2004 |
| WO | 2004/016196 A2 | 2/2004 |
| WO | 2004/091442 A2 | 10/2004 |
| WO | 2004/091443 A2 | 10/2004 |
| WO | 2005/051204 A1 | 6/2005 |
| WO | 2005/122721 A2 | 12/2005 |
| WO | 2005/122954 A1 | 12/2005 |
| WO | 2006/046950 A1 | 5/2006 |
| WO | 2007/014240 A1 | 2/2007 |
| WO | 2007/016698 A2 | 2/2007 |
| WO | 2007/019374 A2 | 2/2007 |
| WO | 2007014240 A1 | 2/2007 |
| WO | 2007016698 A2 | 2/2007 |
| WO | 2007038589 A2 | 4/2007 |
| WO | 2007059199 A2 | 5/2007 |
| WO | 2007/087132 A1 | 8/2007 |
| WO | 2007087132 A1 | 8/2007 |

OTHER PUBLICATIONS

Final Office Action for U.S. Appl. No. 11/686,683, mailed on Jan. 19, 2010, 15 pages.
Non-Final Office Action for U.S. Appl. No. 11/331,777, mailed on Apr. 21, 2008, 11 pages.
Final Office Action for U.S. Appl. No. 11/331,777, mailed on Oct. 14, 2008, 15 pages.
Non-Final Office Action for U.S. Appl. No. 11/331,777, mailed on May 8, 2009, 14 pages.
Final Office Action for U.S. Appl. No. 11/331,777, mailed on Dec. 8, 2009, 16 pages.
Advisory Action for U.S. Appl. No. 11/331,777, mailed on Mar. 10, 2009, 4 pages.
Advisory Action for U.S. Appl. No. 11/331,777, mailed on Feb. 17, 2010, 4 pages.
Non-Final Office Action for U.S. Appl. No. 11/493,148, mailed on Sep. 24, 2008, 12 pages.
Non-Final Office Action for U.S. Appl. No. 11/493,148, mailed on Jun. 5, 2009, 14 pages.
Final Office Action for U.S. Appl. No. 11/493,148, mailed on Dec. 17, 2009, 13 pages.
Non-Final Office Action for U.S. Appl. No. 11/493,148, mailed on Mar. 25, 2010, 14 pages.
Final Office Action for U.S. Appl. No. 11/493,148, mailed on Jul. 12, 2010, 14 pages.
Notice of Allowance for U.S. Appl. No. 11/493,148, mailed on Sep. 30, 2010, 6 pages.
European Office Action for EP Patent Application No. 07716311.1, mailed on Dec. 8, 2009, 3 pages.
Notice of Allowance for U.S. Appl. No. 11/535,901, mailed on Sep. 21, 2010, 26 pages.
"Capio® CL Transvaginal Suture Capturing Device", The Capio CL Transvaginal Suture Capturing Device allows for a transvaginal suture fixation to Cooper's Ligament for Sling Procedures, Boston Scientific, printed on Apr. 7, 2006, 2 pages.
"Capio® CL Transvaginal Suture Capturing Device", Transvaginal Suture Fixation to Cooper's Ligament for Sling Procedures, Boston Scientific, 2000, 4 pages.
"Capio® Open Access and Standard Suture Capturing Devices", Reach, Throw and Capture: One Step. One Device., Boston Scientific, printed on Apr. 7, 2006, 2 pages.
"Capio® RP Suture Device", Boston Scientific, printed on Apr. 7, 2006, 1 page.
"Capio® RP Suture Device", The Capio RP Suturing Device is designed to assist with anastomosis after a radical prostatectomy, undated, 1 page.
"Capio® Suture Capturing Devices", Reach, Throw and Capture: One Step. One Device., Boston Scientific, 2005, 4 pages.
International Search Report for PCT Application No. PCT/FR2004/000765, mailed on Dec. 28, 2004, 10 pages.
International Search Report and Written Opinion of the International Searching Authority received for PCT Application No. PCT/US2007/000190, mailed on Jul. 3, 2007, 9 pages.
International Search Report received for PCT Application No. PCT/AU2004/001674, mailed on Dec. 21, 2004, 3 pages.
International Search Report received for PCT Application No. PCT/FR2004/000766, mailed on Aug. 11, 2004, 9 pages.
International search Report received for PCT Application No. PCT/US2001/031234, mailed on Dec. 14, 2001, 1 page.
International Search Report received for PCT Application No. PCT/US2001/30033, mailed on May 10, 2002, 1 page.
International search report received for PCT Application No. PCT/US2006/028963, mailed on Dec. 6, 2006, 3 pages.
International Search Report received for PCT Application No. PCT/US2007/000190, mailed on Jul. 3, 2007, 5 pages.
International Search Report received for PCT Application No. PCT/US2005/021267, mailed on Nov. 30, 2005, 6 pages.
European Search Report received for EP Patent Application No. EP 01117717, mailed on Apr. 18, 2007, 5 pages.
European Search Report received for EP Patent Application No. EP 90307704, mailed on Apr. 18, 2007, 1 page.
Search report received for French Patent Application No. FR0406352, mailed on Jan. 13, 2005, 3 pages.
European Search Report received for EP Patent Application No. EP 05356101, mailed on Nov. 1, 2005, 2 pages.
Search report received for French Patent Application No. FR 0303893, mailed on Jan. 21, 2004, 2 pages.
Search report received for French Patent Application No. FR 0303895, mailed on Jan. 21, 2004, 3 pages.
International Search Report received for PCT Application No. PCT/US1998/03066, mailed on May 28, 1998, 2 pages.
International Search report received for PCT Application No. PCT/US2004/035329, mailed on Jul. 7, 2005, 7 pages.
Notification Concerning Transmittal of Copy of International Preliminary Report on Patentability (Chapter I of the Patent Cooperation Treaty) issued in corresponding International Application No. PCT/US2007/000190, mailed on Jul. 24, 2008.
International Search Report received for PCT Application No. PCT/US2007/064079 mailed on Aug. 28, 2007, 4 pages.
Final Office Action received for U.S. Appl. No. 11/535,901, mailed on Jan. 29, 2009, 22 pages.
Non-Final Office Action received for U.S. Appl. No. 11/535,901, mailed on Jun. 9, 2009, 22 pages.
Leron, E. et al., "Sacrohysteropexy with synthetic mesh for the management of uterovaginal prolapse", British Journal of Obstetrics and Gynaecology, 108.3, 2001, pp. 629-633.
Final Office Action for U.S. Appl. No. 11/686,683, mailed Nov. 5, 2012, 32 pages.
Non-Final Office Action for U.S. Appl. No. 11/686,683, mailed Aug. 13, 2013, 26 pages.
Non-Final Office Action for U.S. Appl. No. 13/218,840, mailed Jun. 7, 2013, 11 pages.
Non-Final Office Action Response for U.S. Appl. No. 13/218,840, filed Sep. 3, 2013, 9 pages.
Final Office Action Response for U.S. Appl. No. 11/686,683, filed Feb. 5, 2013, 17 pages.

(56) References Cited

OTHER PUBLICATIONS

Pohl, et al, "Bilateral Transvaginal Sacrospinous Colpopexy: Preliminary Experience", 23rd Annual Meeting of the Society of Gynecologic Surgeons, Feb. 24-26, 1997, 7 pages.
Shah, et al, "Short-Term Outcome Analysis of Total Pelvic Reconstruction With Mesh: The Vaginal Approach", The Journal of Urology, vol. 171, Jan. 2004, pp. 261-263.
Hardiman, et al, "Sacrospinous Vault Suspension and Abdominal Colposacropexy: Success Rates and Complications", Section of Urogynecology, Department of Obstetrics and Gynecology, University of Toronto, Mount Sinai Hospital, Sep. 18, 1995, 5 pages.
Non Final Office Action for U.S. Appl. No. 11/331,777, mailed on Dec. 6, 2013, 18 pages.
Response to Non Final Office Action for U.S. Appl. No. 11/331,777, filed Mar. 6, 2014, 8 pages.
Final Office Action for U.S. Appl. No. 11/331,777, mailed on Apr. 14, 2014, 18 pages.
Final Office Action for U.S. Appl. No. 13/218,840, mailed on Dec. 24, 2013, 11 pages.
Response to Final Office Action for U.S. Appl. No. 13/218,840, filed Mar. 24, 2014, 12 pages.
Notice of Allowance for U.S. Appl. No. 13/218,840, mailed on May 1, 2014, 7 pages.
Final Office Action for U.S. Appl. No. 11/686,683, mailed on Feb. 25, 2014, 29 pages.
Response to Non Final Office Action for U.S. Appl. No. 11/686,683, filed Nov. 13, 2013, 13 pages.
Response to Office Action for European Patent Application No. 07758616.2, filed on Oct. 17, 2011, 31 pages.
Office Action for European Patent Application No. 06815573.8, mailed on Nov. 15, 2013, 3 pages.
International Preliminary Report on Patentability for PCT Application No. PCT/US2011/49753, mailed on Mar. 14, 2013, 9 pages.
Extended European Search Report for EP Application No. 13164488.2, mailed Jul. 31, 2014, 6 pages.
Non-Final Office Action for U.S. Appl. No. 13/606,883, mailed Aug. 1, 2014, 18 pages.
Notice of Allowance for U.S. Appl. No. 13/218,840, mailed Aug. 15, 2014, 7 pages.
Non-Final Office Action for U.S. Appl. No. 11/686,683, mailed Jun. 17, 2014, 31 pages.
Response to Final Office Action for U.S. Appl. No. 11/686,683, filed May 23, 2014, 15 pages.
Response to Final Office Action for U.S. Appl. No. 11/331,777, filed Jul. 11, 2014, 13 pages.
Non-Final Office Action for U.S. Appl. No. 11/331,777, dated Sep. 29, 2014, 19 pages.
Response to Non-Final Office Action for U.S. Appl. No. 11/331,777, filed Dec. 26, 2014, 7 pages.
Final Office Action for U.S. Appl. No. 11/331,777, mailed on Mar. 3, 2015, 14 pages.
Final Office Action for U.S. Appl. No. 11/686,683, mailed on Dec. 23, 2014, 18 pages.
Response to Final Office Action for U.S. Appl. No. 11/686,683, filed Feb. 23, 2015, 12 pages.
Notice of Allowance for U.S. Appl. No. 11/686,683, mailed on Mar. 13, 2015, 7 pages.
Final Office Action for U.S. Appl. No. 13/606,883, mailed on Mar. 30, 2015, 23 pages.

* cited by examiner

APPARATUS AND METHOD FOR SUSPENDING A UTERUS

CROSS REFERENCE TO RELATED APPLICATIONS

This application is a continuation of, and claims priority to, U.S. patent application Ser. No. 11/535,901, filed on Sep. 27, 2006, entitled "APPARATUS AND METHOD FOR SUSPENDING A UTERUS," which, in turn, claims priority to U.S. Provisional Application No. 60/721,366, filed on Sep. 28, 2005, entitled "APPARATUS AND METHOD FOR SUSPENDING A UTERUS," both of which are incorporated by reference herein in their entirety.

BACKGROUND

The present invention relates generally to the field of medical devices, and in particular to an apparatus and method for suspending a uterus of a human or animal subject.

Many women with uterine prolapse would like for their condition to be surgically corrected, but avoid or delay undergoing an operation because they wish to avoid hysterectomy. The potential reasons for avoiding hysterectomy vary widely including plans for future childbearing, concern about the invasiveness of the procedure or the difficulty of the recuperation, or fear of diminished sexual function. Some women are simply reluctant to "give up" this part of their body so closely associated with their reproductive health, childbearing, and femininity.

Uterine prolapse can be effectively treated without hysterectomy, with low morbidity and high rates of patient satisfaction. A properly performed uterine suspension surgery often results in a significantly better anatomic outcome than hysterectomy. Yet, many hysterectomy procedures are performed for pelvic prolapse. One reason why most patients remain unaware of the uterine-sparing option is because with the exception of a few dedicated sub-specialists, most surgeons receive no training in these techniques. In addition, known techniques and equipment can be difficult and require involved specialized training that many general practitioners have not undertaken.

Thus a need exists for an improved apparatus and method for providing a minimally invasive hysteropexy that can be incorporated into mainstream gynecologic practice.

SUMMARY OF THE INVENTION

An apparatus, method and kit for performing a uterine suspension procedure are disclosed herein. In one embodiment, an inter-vaginal device for performing a uterine suspension includes a rigid body for manipulating the uterus and implanting a suspension member, such as a mesh, for securing the uterus to an anchoring site (e.g., into a pelvic muscle or ligament). In another embodiment, a method includes inserting at least a portion of a uterine suspension member through an anterior or posterior vaginal incision. An end of the suspension member is anchored to a selected portion of a pelvic tissue with anchoring methods that may include tying off with sutures, or directly affixing the suspension member to the pelvic tissue with, for example, self-affixing mesh arms. At least a portion of the suspension member can be attached to a vaginal apex or adjacent to the vaginal apex to further facilitate scarring. A uterine manipulator can be advanced in a direction toward the selected portion of the pelvic tissue such that at least a portion of a uterus is moved upward.

DETAILED DESCRIPTION

Figure 1:
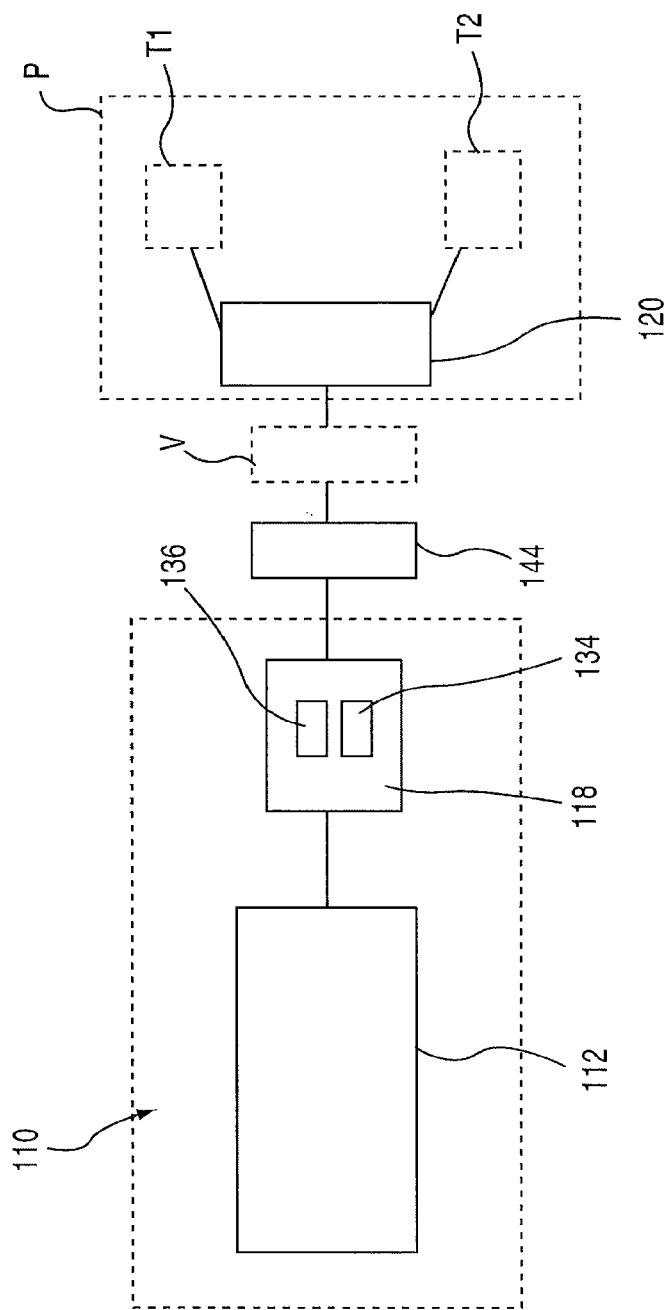
FIG. 1 is a schematic illustration of various components that can be used in a method according to an embodiment of the invention.

The invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

In some embodiments, the invention includes a device for performing a uterine suspension comprising a substantially rigid body having a handle at a distal end thereof; a lumen through the substantially rigid body for housing sutures of a suspension member; and a uterine manipulator at a proximal end thereof. The uterine manipulator can further include a prong for insertion into the uterus; a tenaculum clip for securing the uterine manipulator to the cervix; and a pair of wings for aiding in securing the suspension member to the vagina. Optionally, the uterine suspension device can be included in a kit, along with a mesh or graft for a cystocele and/or a rectocele augmentation.

In another embodiment the invention includes a method of performing a uterine suspension. The method can include the steps of making an anterior or posterior vaginal incision; palpating ischial spines bilaterally; inserting the suspension member through the vaginal incision; placing suspension sutures of the suspension member or a portion of the suspension member (e.g., self-affixing tanged mesh) into a sacrospinous or iliococcygeus anchoring site; inserting the uterine manipulator through the cervix and securing it thereto; fastening the suspension member to the corners of the vaginal apex or placing the suspension member adjacent to the vaginal apex; applying gentle traction on the sutures or the self-affixing mesh; advancing the uterine manipulator to the anchoring site; removing the device; tying the sutures or adjusting the self-affixing mesh to the appropriate tension; and closing the vaginal incision.

In still another embodiment, the invention includes a suspension member, the suspension member includes at least one suture having an anchoring member at a first end and a free end for manipulation by a practitioner, wherein the suture is woven through the suspension member for providing accordion-type folds. In some embodiments, the suspension member is constructed of a self-affixing mesh material requiring passage of mesh arms rather than sutures through the pelvic tissue/anchoring site.

Advantageously, the device of the invention will introduce a minimally invasive, uterinesparing prolapse surgery that can be incorporated into mainstream gynecologic practice. The device can provide an effective, simple and reproducible uterine suspension technique for general gynecologic surgeons. The procedures described herein have the potential to attract countless women with uterine prolapse who would otherwise have avoided an operation, and increase the market of women choosing the described surgery for treatment of their prolapsed condition.

These and other aspects, features and advantages of the invention will be understood with reference to the drawing figures and detailed description herein, and will be realized by means of the various elements and combinations particularly pointed out in the appended claims. It is to be understood that both the foregoing general description and the brief description of the drawings and detailed description of the invention are exemplary and explanatory of some embodiments of the invention, and are not restrictive of the invention, as claimed.

FIG. 1 is a schematic illustration of various components that can be used in a uterine suspension procedure to treat, for example, a uterine prolapse. A suspension device 110 can include a body 112 having a uterine manipulator device 118 disposed at a proximal end of the body 112. The suspension device can be, for example, a suspension device 10 described in more detail with reference to FIG. 2. In some embodiments, the body 112 is substantially rigid and defines a lumen (not shown in FIG. I) extending between a proximal end and a distal end of the body 112. The uterine manipulator device 118 can include, for example, a prong 134 configured to be inserted through a cervix, and a clip 136, such as a tenaculum clip, with a sharp point configured to secure the uterine manipulator device 118 to the cervix during a uterine suspension procedure, as will be described in more detail below with reference to the uterine manipulator 18.

The suspension device 110 can be used to help secure a uterine suspension member 120 within a pelvic region P of a patient. A suspension member 120 can be formed, for example, with a mesh material and configured to be anchored on one end to a pelvic tissue T1 such as a sacrospinous ligament or a levator muscle, such as the iliococcygeus muscle, and on another end to a pelvic tissue T2 disposed on an opposite side of the uterus of the patient. Another portion of the suspension member 120 can be configured to be attached to a vaginal apex V of the patient. An example embodiment of a suspension member 20 is described in more detail below with reference to FIG. 2. An anchoring member 144 that includes a pair of winged portions (not shown in FIG. 1) can be releasably coupled to the uterine manipulator 118 of the suspension device 110 and inserted into a vagina of the patient using the suspension device 110. An example embodiment of an anchoring member 44 is described below with reference to FIG. 2. The anchoring member 144 can be released from the suspension device 120 and used to help secure the suspension member 120 within the pelvic region P of the patient. The suspension device 110 can also be used to move or manipulate the uterus during a uterine suspension procedure to place the uterus into a correct anatomical position.

Figure 2:
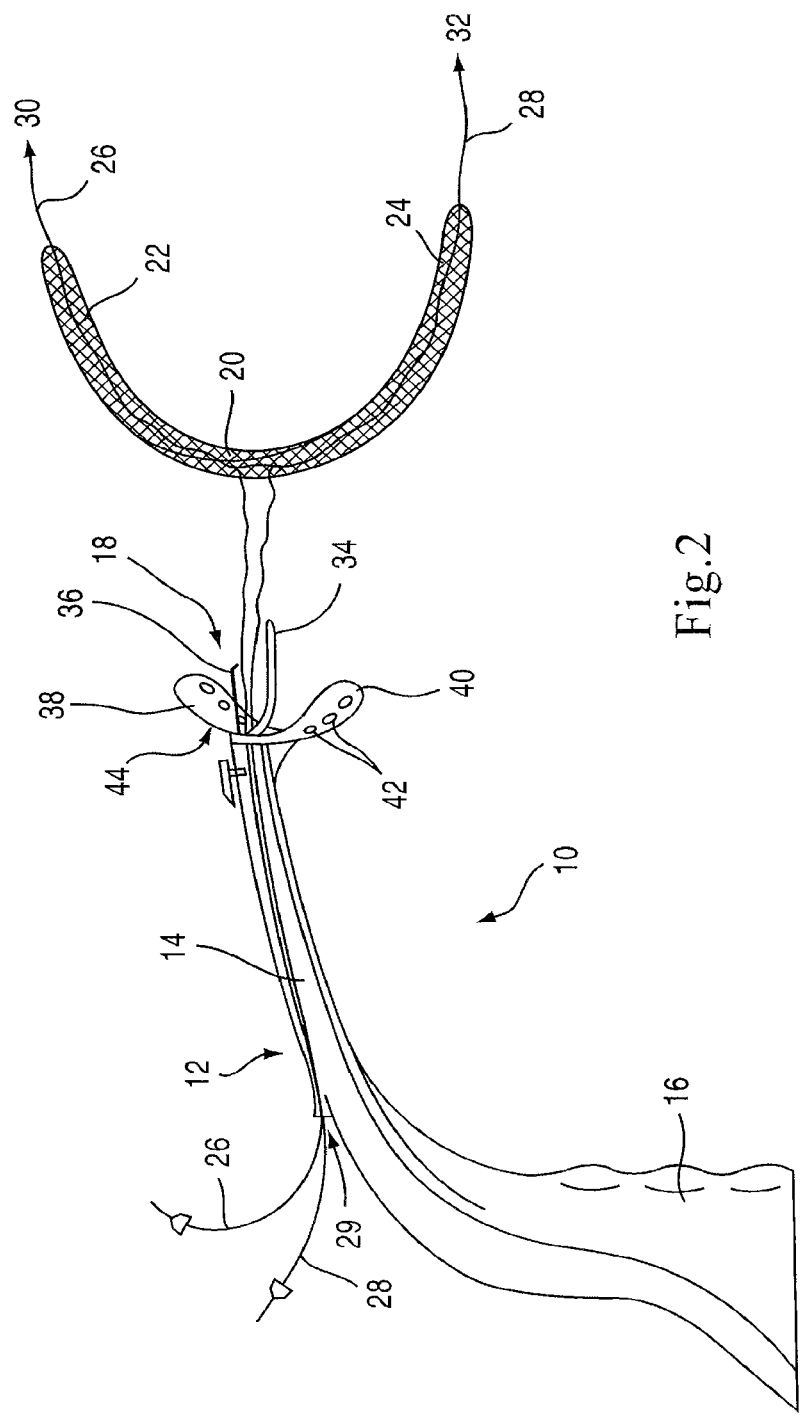
FIG. 2 is a side perspective view of a device for performing a uterine suspension and a uterine suspension member according to an embodiment of the invention.

With reference now to FIG. 2, an inter-vaginal uterine suspension device 10 for performing a vaginal hysteropexy is shown by way of an example embodiment. The uterine suspension device 10 includes a substantially rigid body 12 having a shaft 14 with a handle 16 at its distal end and a uterine manipulator portion 18 at its proximal end. Preferably, the handle 16 is an ergonomic handle, and those skilled in the art will understand that various handles can be employed without deviating from the scope of the present invention.

The substantially rigid body 12 is used to implant a suspension member 20 around the uterus so as to secure the uterus to a muscle or ligament in the deep pelvic area. The body 12 can be constructed of an inert and biocompatible material such as, for example, a metal such as titanium or stainless steel or a plastic, although those skilled in the art will understand that various materials can be employed without deviating from the scope of the present invention. The rigid body 12 can be reusable or it can be disposable. If the body is reusable, then the materials of construction are preferably autoclavable or otherwise capable of sterilization.

The suspension member 20 is configured generally in the shape of a "U" having a pair of arms 22 and 24. The suspension member 20 can be formed, for example, of polypropylene or prolene mesh, although those skilled in the art will understand that various other biocompatible and biologically inert materials can be used as well for the suspension member 20. Additionally, the suspension member 20 may not be a "mesh" but instead be a band of an inert and biologically compatible material.

At least one, and preferably two tensioning sutures 26 and 28 are woven into the suspension member 20 for providing a suspension member with an accordion-type design (or accordion-type folds). A first anchor 30 is located at the proximal end of the suture 26, and a second anchor 32 is located at the proximal end of the suture 28. The anchors 30 and 32 anchor or attach the sutures 26 and 28 to an anchoring site, which is typically a pelvic muscle or ligament. The distal ends of the pair of sutures 26 and 28 are woven into the suspension member 20 and pass through a lumen 29 through the shaft 14 and out of the body 12 of the device 10 near the handle 16 so that the practitioner can manipulate the sutures with one hand while gripping the handle 16 with the other hand to manipulate the uterus.

The uterine manipulator portion 18 can include a substantially rigid prong 34 for insertion through the cervix into the uterus, a tenaculum (or a tenaculum clip) 36 with a sharp point for securing the uterine manipulator to the cervix, and an anchoring member 44 having a pair of wings 38 and 40 for anchoring the suspension member 20 to the vagina, can be coupled to the uterine manipulator 18. The wings 38 and 40 can be constructed of a malleable, "shapememory" plastic, which allows for a comfortable fit into the vaginal fornices. Also, the wings 38 and 40 can each include at least one, and in some embodiments, a plurality of apertures 42 therein so that the practitioner can connect or suture the suspension member 20 to the vagina through the apertures. The wings 38 and 40 spread into the lateral corners of the vagina so that the suspension member 20 can be secured to the vagina.

Figure 3:
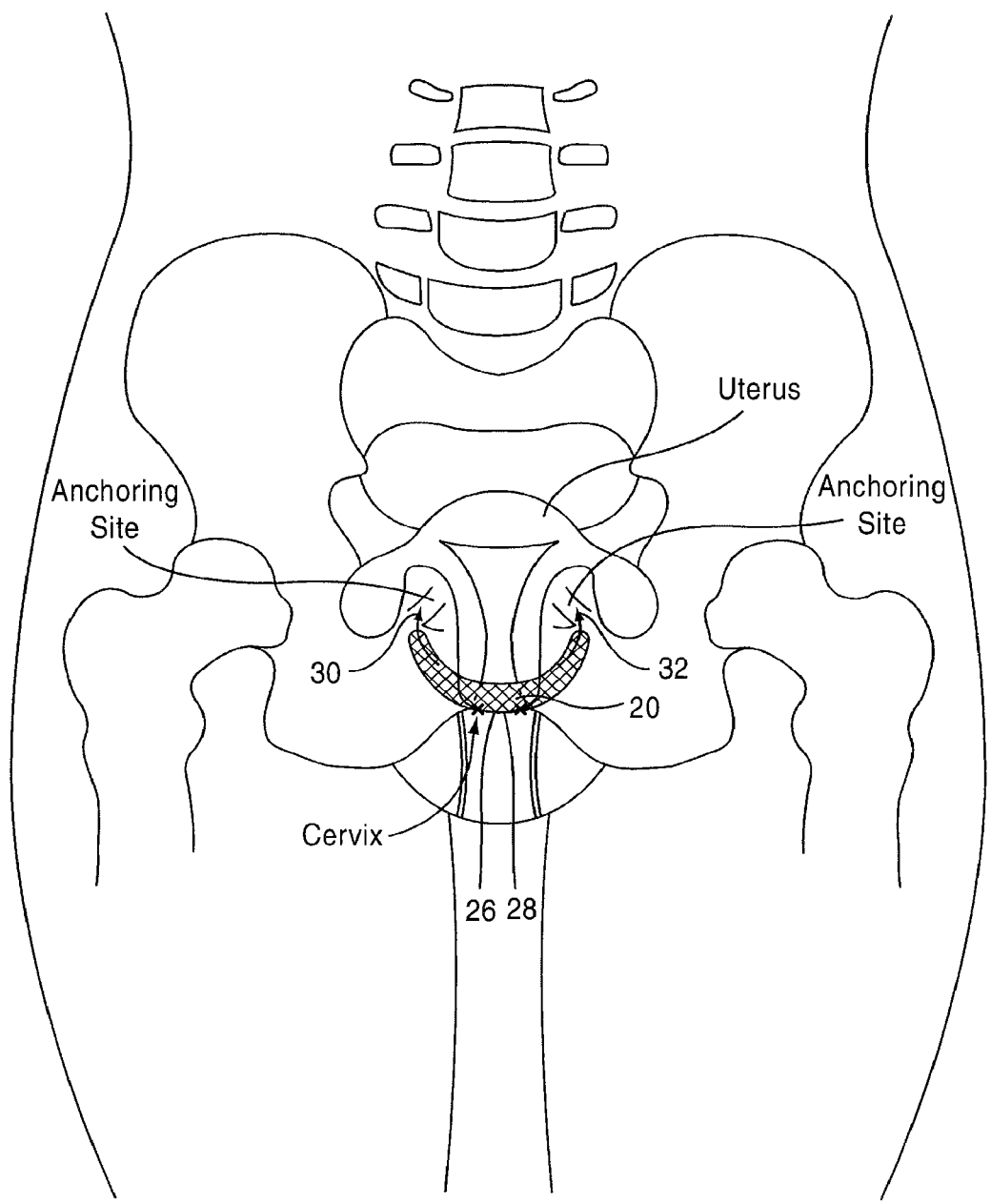
FIG. 3 is a front pictorial representation of a placement of a suspension member around a uterus using the device of FIG. 2.

In one embodiment, a method of performing a vaginal uterine suspension begins by administering anesthesia to the patient. For example, either a general anesthesia or an epidural anesthesia can be used. A practitioner makes an anterior or posterior vaginal incision, performs a standard anterior colporrhaphy dissection, and palpates the ischial spines bilaterally, all of which are generally well known to those skilled in the art. As the uterine suspension device 10 is inserted into the vagina, the practitioner inserts the suspension member 20 through the anterior (or posterior) vaginal incision. The ends of the suspension member 20, i.e., the sutures 26 and 28, are anchored in a pelvic muscle or ligament such that the suspension member generally surrounds the uterus. In some embodiments, the first suture 28 with anchor 32 is anchored into the sacrospinous ligament or the levator muscle (such as the iliococcygeus muscle) and the second suture 26 with anchor 30 is anchored into the sacrospinous or levator muscle on the opposite side, as depicted in FIG. 3. For example, the Capio® device manufactured by Boston Scientific can be used to place the sutures, although those skilled in the art will understand that various other suturing devices and techniques can be employed as well, including using a needle trocar to perforate the muscle or ligament and anchor the suture, or attach the suspension device 20 directly to the muscle. For example, the suspension device 20 can be formed with a mesh material that can be anchored directly to the tissue or muscle. Some iterations may involve fixation of mesh arms with no sutures/knot tying, by passing tension-free self-affixing mesh through the tissue or muscle.

The prong 34 of the uterine manipulator 18 is inserted through the cervix into the uterus and is fastened thereto with the tenaculum clip 36. In so doing, the wings 38 and 40 coupled to the device 10 are positioned into the lateral corners of the vaginal apex. The suspension member 20 is fastened to the corners of the vaginal apex by suturing the suspension member 20 to the inside of the vagina through the apertures 42 in the wings 38 and 40. For example, sutures can be placed 2 cm lateral to the midline on each side. Optionally, the practitioner can use bioabsorbable anchors or sutures to secure the suspension member 20 to the vagina. Also optionally, if an augmentation is planned, an anterior or posterior graft can be secured with the same anchors at the vaginal apical corners.

The practitioner applies gentle traction on the sutures 26 and 28 (i.e., pulling the sutures rearwardly from the device 10) while simultaneously slowly advancing the uterine manipulator 18 in a direction generally towards the anchoring site e.g., the sacrospinous ligament or the iliococcygeus muscle). In so doing, the cervix along with the uterus is pushed up while the suspension member 20 shortens because of its accordion design and recreates the cardinaluterosacral attachments between the vaginal apex and the pelvic sidewall. The practitioner removes the device 10, withdrawing it over the sutures 26 and 28, which are held at constant tension. The practitioner ties the sutures 26 and 28, without tension, leaving them inside the vaginal incision. The vagina is closed after completion of anterior compartment repair (i.e. colporrhaphy, graft placement).

Figure 4:
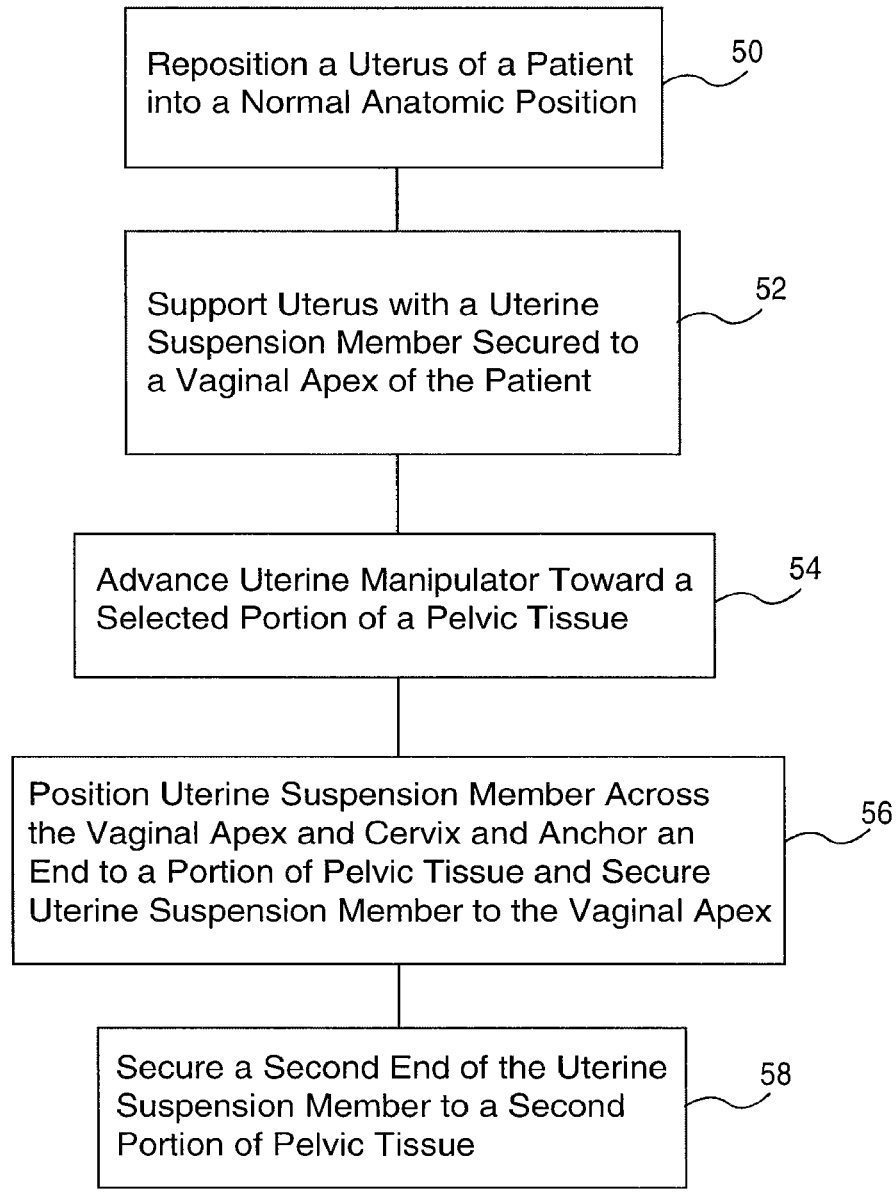
FIG. 4 is a flowchart illustrating a method according to an embodiment of the invention.

FIG. 4 illustrates a method according to an embodiment of the invention. A method includes at 50 repositioning a uterus of a patient into a normal anatomic position. At 52, the uterus is supported in the normal anatomic position with a uterine suspension member secured to a vaginal apex of the patient. In some embodiments, the repositioning of the uterus includes at 54, advancing a uterine manipulator in a direction toward a selected portion of a pelvic tissue such that at least a portion of the uterus is moved upward. In some embodiments, the uterine suspension member is positioned across the vaginal apex and an end of the uterine suspension member is anchored or secured to a portion of pelvic tissue, and the uterine suspension member is also secured to the vaginal apex, at 56. In some embodiments, a first end of the uterine suspension member is secured to a first portion of pelvic tissue and a second end of the uterine suspension member is secured to a second portion of pelvic tissue, at 58. In some embodiments, an end of the uterine suspension member is secured to a sacrospinous ligament. In some embodiments, the uterine suspension member is positioned around the uterus and secured to a levator muscle.

Figure 5:
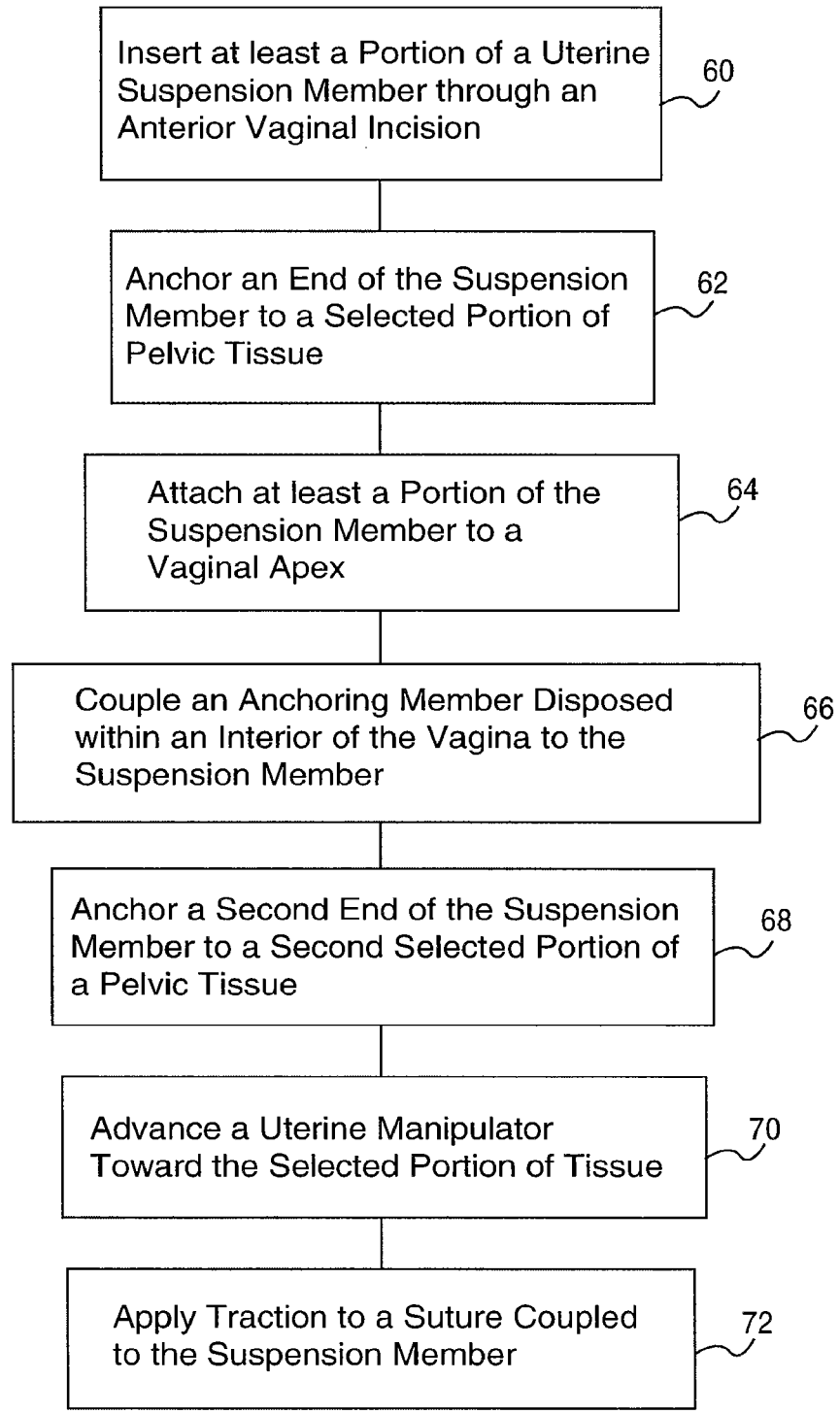
FIG. 5 is a flowchart illustrating a method according to another embodiment of the invention.

FIG. 5 illustrates a method according to another embodiment of the invention. A method includes at 60 inserting at least a portion of a uterine suspension member through an anterior or posterior vaginal incision. An end of the suspension member is anchored to a selected portion of a pelvic tissue at 62. The pelvic tissue can be, for example, a sacrospinous ligament, or a levator muscle, such as an iliococcygeus muscle. In some embodiments, the anchoring an end of the suspension member includes anchoring an end of a suture coupled to the suspension member to the selected portion of the pelvic tissue.

At 64, at least a portion of the suspension member is attached to a vaginal apex. In some embodiments, the attaching the at least a portion of the suspension member to the vaginal apex includes at 66, coupling an anchoring member disposed within an interior of the vagina to the suspension member such that a portion of a wall of the vagina is disposed between the suspension member and the anchoring member. In some embodiments, the attaching at least a portion of the suspension member to the vaginal apex includes attaching the suspension member at a first corner of the vaginal apex and attaching the suspension member at a second corner of the vaginal apex. In some embodiments, the suspension member has a first end and a second end, and the second end of the suspension member is anchored to a second selected portion of a pelvic tissue on an opposite side of the uterus at 68.

At 70, a uterine manipulator can be optionally advanced in a direction toward the selected portion of tissue such that at least a portion of a uterus is moved upward. At 72, in some embodiments, simultaneously with the advancing the uterine manipulator, traction is applied to a suture coupled to the suspension member.

In some embodiments, a kit can be provided that includes at least one suspension member, such as suspension member 20, and a medical device, such as suspension device 10. The suspension member can have an end configured to be anchored to a pelvic tissue within a patient and a portion configured to be attached to a vaginal apex of the patient. The medical device can be used during a uterine suspension procedure to assist in securing the suspension member within a pelvic region of the patient. A kit can also include an anchoring member, such as anchoring member 44, configured to be disposed within an interior of a vagina of the patient and coupleable to the suspension member to help secure the suspension member to the vagina. A kit can also include at least one mesh or a graft to be used in a procedure such as a cystocele or rectocele augmentation.

CONCLUSION

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents.

The previous description of the embodiments is provided to enable any person skilled in the art to make or use the invention. While the invention has been particularly shown and described with reference to embodiments thereof, it will be understood by those skilled in art that various changes in form and details may be made therein without departing from the spirit and scope of the invention.

For example, a variety of different suspension members 20 can be used in any of the uterine suspension procedures described herein. A suspension member can be a variety of different configurations, shapes and/or sizes and be formed with various different materials not specifically described. The suspension device 10 can include any combination or subcombination of the various features and components described herein. Further, other configurations for a suspension device can be used to perform the uterine suspension procedures described herein, while still remaining within the scope of the invention.

What is claimed is:

1. A method, comprising:
   inserting at least a portion of a uterine suspension member through an anterior vaginal incision of a patient;
   positioning the uterine suspension member such that the uterine suspension member forms a "U" shape and generally surrounds a uterus of the patient;
   anchoring an end of the suspension member to a selected portion of a pelvic tissue, the anchoring including inserting a portion of the uterine suspension member through the pelvic tissue; and
   securing at least a portion of the suspension member to a vaginal apex.

2. The method of claim 1, further comprising:
   advancing a uterine manipulator in a direction toward the selected portion of the pelvic tissue such that at least a portion of a uterus is moved upward.

3. The method of claim 1, wherein the end of the suspension member is a first end, the selected portion of a pelvic tissue is a first selected portion of a pelvic tissue, the method further comprising:
   prior to the securing, anchoring a second end of the suspension member to a second selected portion of a pelvic tissue on an opposite side of a uterus.

4. The method of claim 1, wherein the securing the at least a portion of the suspension member to the vaginal apex includes coupling an anchoring member disposed within an interior of the vagina to the suspension member such that a portion of a wall of the vagina is disposed between the suspension member and the anchoring member.

5. The method of claim 1, wherein the securing the at least a portion of the suspension member to the vaginal apex, includes securing the suspension member at a first corner of the vaginal apex and securing the suspension member at a second corner of the vaginal apex.

6. The method of claim 1, further comprising:
   advancing a uterine manipulator in a direction toward the selected portion of the pelvic tissue such that at least a portion of a uterus is moved upward; and simultaneously with the advancing the uterine manipulator, applying traction to a suture.

7. The method of claim 1, wherein the pelvic tissue includes a sacrospinous ligament of the patient.

8. The method of claim 1, wherein the inserting a portion of the uterine suspension member through the pelvic tissue includes inserting a self-affixing portion of the uterine suspension member through a sacrospinous ligament of the patient.

9. The method of claim 1, wherein the inserting a portion of the uterine suspension member through the pelvic tissue includes inserting a self-affixing portion of the uterine suspension member through the pelvic tissue using a suturing device.

10. The method of claim 1, wherein the inserting a portion of the uterine suspension member through the pelvic tissue includes using a suturing device to insert the portion of the uterine suspension member through the pelvic tissue.

11. An apparatus, comprising:
    a body having a proximal end and a distal end, the proximal end of the body configured to be inserted into a vagina of a patient to assist in securing a uterine suspension member within a pelvic region of the patient,
    the body defining a lumen and a first opening on the distal end of the body and a second opening on the proximal end of the body, the first and second opening being in communication with the lumen,
    the lumen configured to receive a suture coupled to a suspension member that is disposed within a pelvic region of the patient through the second opening such that an end of the suture is disposed through the first opening and accessible outside the lumen; and
    a uterine manipulator disposed at the proximal end of the body, the uterine manipulator configured to be releasably coupled to a cervix of the patient during a uterine suspension procedure, the uterine manipulator having an anchoring member having a first wing portion and a second wing portion, the first wing portion defining an opening, the second wing portion defining an opening.

12. The apparatus of claim 11, wherein the uterine manipulator includes a prong for insertion through the cervix and into a uterus of the patient, and a clip for securing the uterine manipulator to the cervix.

13. The apparatus of claim 11, wherein the body is configured to releasably couple an anchoring member at the proximal end of the body such that the anchoring member can be released from the body at a location within an interior of the vagina to help secure a uterine suspension member to the vagina.

* * * * *